US 6,689,117 B2

United States Patent
Sweeney et al.

(10) Patent No.: US 6,689,117 B2
(45) Date of Patent: Feb. 10, 2004

(54) DRUG DELIVERY SYSTEM FOR IMPLANTABLE MEDICAL DEVICE

(75) Inventors: Robert J. Sweeney, Woodbury, MN (US); Avram Scheiner, Vadnais Heights, MN (US); Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 128 days.

(21) Appl. No.: 09/740,129

(22) Filed: Dec. 18, 2000

(65) Prior Publication Data

US 2002/0077620 A1 Jun. 20, 2002

(51) Int. Cl.[7] .................. A61M 31/00; A61K 9/22; A61N 1/18; A61N 1/20
(52) U.S. Cl. ............... 604/503; 604/66; 604/890.1; 604/65; 600/547; 607/3; 607/60
(58) Field of Search ............... 607/32, 30, 57, 607/60, 3–6; 604/891.1, 890.1, 65–67, 503; 128/DIG. 12, DIG. 13; 600/547

(56) References Cited

U.S. PATENT DOCUMENTS

| 3,692,027 A | 9/1972 | Ellinwood, Jr. ............. 128/260 |
| 4,003,379 A | 1/1977 | Ellinwood, Jr. ............. 128/260 |
| 4,146,029 A | 3/1979 | Ellinwood, Jr. ............. 128/260 |
| 4,281,664 A | 8/1981 | Duggan ....................... 128/696 |
| 4,299,220 A | 11/1981 | Dorman ....................... 128/260 |
| 4,544,371 A | 10/1985 | Dormandy, Jr. et al. .... 604/891 |
| 4,556,063 A | 12/1985 | Thompson et al. .... 128/419 PT |
| 4,871,351 A | 10/1989 | Feingold ....................... 604/66 |
| 4,897,987 A | 2/1990 | Spalla ......................... 56/16.7 |
| 4,944,299 A | 7/1990 | Silvian ................... 128/419 PG |
| 4,987,897 A | * 1/1991 | Funke .......................... 607/32 |
| 5,040,533 A | 8/1991 | Fearnot ................. 128/419 PG |
| 5,041,107 A | 8/1991 | Heil, Jr. .................... 604/891.1 |
| 5,042,497 A | 8/1991 | Shapland ..................... 128/696 |
| 5,058,581 A | 10/1991 | Silvian ................. 128/419 PG |
| 5,087,243 A | 2/1992 | Avitall ......................... 604/20 |
| 5,127,404 A | 7/1992 | Wyborny et al. ........ 128/419 P |
| 5,190,035 A | 3/1993 | Salo et al. ................... 128/419 |
| 5,220,917 A | 6/1993 | Cammilli et al. ....... 128/419 D |
| 5,269,301 A | 12/1993 | Cohen ........................... 607/6 |
| 5,305,745 A | 4/1994 | Zacouto ...................... 128/637 |
| 5,342,408 A | 8/1994 | deCoriolis et al. ............ 607/32 |
| 5,368,028 A | * 11/1994 | Palti ............................ 604/522 |
| 5,416,695 A | 5/1995 | Stutman et al. ........ 364/413.02 |
| 5,456,692 A | 10/1995 | Smith, Jr. et al. ............. 607/31 |
| 5,460,605 A | 10/1995 | Tuttle et al. .................. 604/67 |
| 5,496,360 A | 3/1996 | Hoffmann et al. .......... 607/120 |
| 5,551,953 A | 9/1996 | Lattin et al. .................. 604/20 |
| 5,556,421 A | 9/1996 | Prutchi et al. ................ 607/36 |
| 5,562,713 A | 10/1996 | Silvian ........................ 607/32 |
| 5,579,876 A | 12/1996 | Adrian et al. .......... 188/322.17 |
| 5,586,556 A | 12/1996 | Spivey et al. ............... 128/697 |

(List continued on next page.)

FOREIGN PATENT DOCUMENTS

EP 0054138 10/1981 ......... C08F/210/02

*Primary Examiner*—Michael J. Hayes
*Assistant Examiner*—Matthew DeSanto
(74) *Attorney, Agent, or Firm*—Schwegman, Lundberg, Woessner & Kluth, P.A.

(57) ABSTRACT

A drug delivery system and method in which an implantable medical device communicates with and controls an external drug delivery device with low energy potential signals. The implantable device generates potential signals modulated with digitally encoded command information by operating a current source to cause corresponding electrical potentials that can be sensed at the skin surface by the external drug delivery device. The drug delivery device then demodulates the sensed potentials and decodes the digital data to extract command information therefrom to deliver a drug accordingly.

11 Claims, 3 Drawing Sheets

U.S. PATENT DOCUMENTS

| | | | |
|---|---|---|---|
| 5,607,418 A | 3/1997 | Arzbaecher | 604/891.1 |
| 5,690,682 A | 11/1997 | Buscemi et al. | 607/3 |
| 5,693,075 A | 12/1997 | Plicchi et al. | 607/17 |
| 5,720,770 A | 2/1998 | Nappholz et al. | 607/30 |
| 5,730,125 A | 3/1998 | Prutchi et al. | 128/637 |
| 5,836,935 A | 11/1998 | Ashton et al. | 604/891.1 |
| 5,893,881 A | 4/1999 | Elsberry et al. | 607/5 |
| 5,899,928 A * | 5/1999 | Sholder et al. | 607/32 |
| 5,925,066 A | 7/1999 | Kroll et al. | 607/3 |
| 6,115,636 A | 9/2000 | Ryan | 607/60 |
| 6,453,195 B1 | 9/2002 | Thompson | 607/3 |

* cited by examiner

DRUG DELIVERY SYSTEM FOR IMPLANTABLE MEDICAL DEVICE

FIELD OF THE INVENTION

This invention pertains to implantable medical devices such as cardiac pacemakers and implantable cardioverter/defibrillators. In particular, the invention relates to a system and method enabling an implantable medical device to communicate with and control an external drug delivery device.

BACKGROUND

Implantable medical devices are commonplace today, particularly for treating cardiac dysfunction. Cardiac pacemakers, for example, are implantable medical devices that replace or supplement a heart's compromised ability to pace itself (i.e., bradycardia) due to chronotropic incompetence or a conduction system defect by delivering electrical pacing pulses to the heart. Implantable cardioverter/defibrillators (ICD's) are devices that deliver electrical energy to the heart in order to reverse excessively rapid heart rates (tachycardia) including life threatening cardiac arrhythmias such as ventricular fibrillation. Since some patients have conditions that necessitate pacing and also render them vulnerable to life-threatening arrhythmias, implantable cardiac devices have been developed that combine both functions in a single device.

Most pacemakers today are operated in some sort of synchronous mode where the pacing pulses are delivered in a manner that is dependent upon the intrinsic depolarizations of the heart as sensed by the pacemaker. ICD's must also sense the electrical activity of the heart in order to detect an arrhythmia that will trigger delivery of the shock pulse in an attempt to reverse the condition. Such sensing information can be used to initiate another mode of therapy, and efforts have been made in the past to combine automatic drug delivery by an implantable drug delivery system with either pacemakers, ICD's, or both in order to treat cardiac arrhythmias.

Implantable drug delivery systems suffer from a number of disadvantages, however, when compared with an external drug delivery device. Although the drug reservoir of an implantable delivery device can be replenished, it is difficult to change the drug once it is put into the reservoir, making patient management difficult in cases where a patient's condition either changes or otherwise requires a change of medication. In addition, drugs degrade over time. Finally, there is the risk of leakage from the implanted reservoir, the consequences of which can range from an annoyance to a medical emergency. For these reasons, drug delivery from an external device is preferred in many situations.

In order to control the delivery of drugs or other therapies by an external device, the implanted device must be capable of transmitting command and control information to the external device. This is the primary problem with which the present invention is concerned.

SUMMARY OF THE INVENTION

The present invention relates to a drug delivery system and method in which an implantable medical device communicates with and controls an external drug delivery device with low energy potential signals. The implantable device generates potential signals by operating a current source to cause corresponding electrical potentials that can be sensed at the skin surface by the external drug delivery device. The current source is operated so as to generate a carrier waveform that can be modulated with digitally encoded command information. The external drug delivery device includes electrodes at the skin surface for sensing potentials and circuitry for demodulating the sensed carrier waveform. The drug delivery device may then decode the digital data to extract command information therefrom and deliver a drug accordingly.

In accordance with the invention, the carrier waveform is digitally modulated with the digitally encoded information by varying the amplitude or frequency of the carrier waveform using, for example, amplitude shift-keying or frequency shift-keying. In a particular embodiment, a digital pulse train is modulated with the digitally encoded information by varying the frequency, width, or position of the pulses. The pulse train is then used to amplitude modulate the carrier waveform.

Certain implantable medical devices, such as rate-adaptive pacemakers, may use an impedance technique for measuring minute ventilation and/or cardiac stroke volume. In that technique, an oscillating current is made to flow between two electrodes located within the thorax, and the impedance between the electrodes is measured. In accordance with the invention, the impedance measuring current may be used as the carrier waveform and modulated with digitally encoded information by the implantable device for transmission to the external drug delivery device.

The present invention may be incorporated into a system where the implantable device is a cardiac device such as an implantable cardioverter/defibrillator, cardiac pacemaker, or combination device. A dose of a drug is then delivered by the drug delivery device to a patient upon detection of a particular medical condition such as an arrhythmia. In one embodiment, the drug delivery device is an electrically modulated transdermal drug delivery device designed for external affixation to a patient's skin surface at a suitable location. The electrically modulated transdermal delivery injector may have one electrode with a drug reservoir in contact with the skin, another electrode also contacting the skin, and a voltage source for imposing a voltage between the electrodes. The drug delivery device also has a data communications interface for receiving command signals from the implantable cardiac device, and circuitry for controlling the delivery of the drug in accordance with the command signal.

DESCRIPTION OF A SPECIFIC EMBODIMENT

Figure 1:
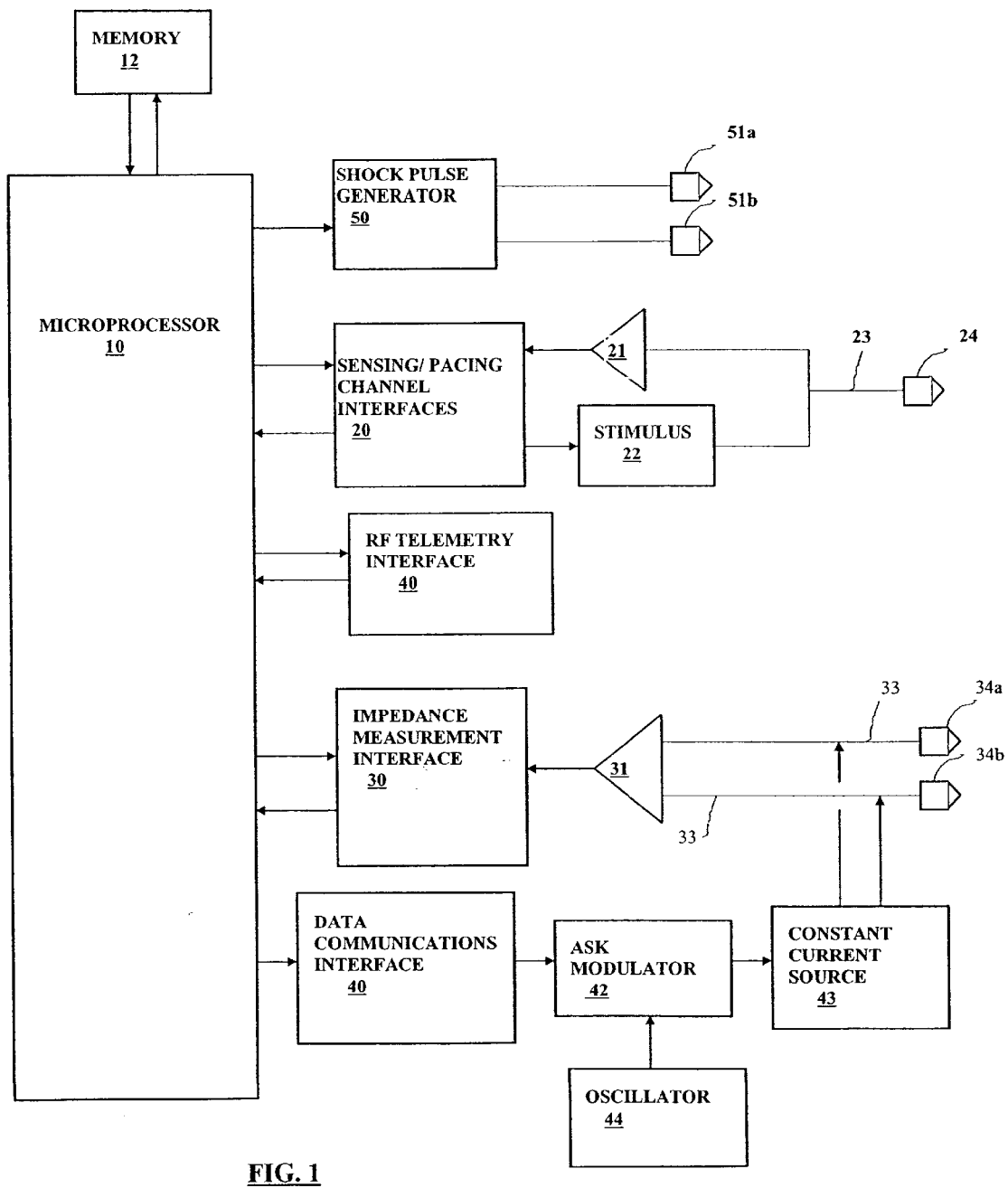
FIG. 1 is a system diagram of an exemplary implantable cardiac device.

The present invention is embodied by a drug delivery system in which an implantable medical device capable of sensing a physiological variable or event controls the delivery of a drug from an external delivery device in response to the sensed variable. In the particular embodiment described below in detail, the implantable medical device is a cardiac device such as an implantable cardioverter/defibrillator, pacemaker, or combination device. Among the physiological variables that can be sensed by such a device and used to control the delivery of drugs are heart rhythm, cardiac output, ventilation rate, and myocardial perfusion (i.e., detection of ischemia). When a particular medical condition occurs, such as an arrhythmia or ischemic episode, the cardiac device transmits a command signal to an external drug delivery device that causes the delivery of a specified amount of drug in an attempt to treat the condition. The delivery device preferably delivers the drug transdermally, but alternate embodiments may employ an instrument with circulatory access such as an intravenous line or hypodermic needle.

Command information is transmitted from the implantable device to the drug delivery device via a carrier waveform sensed by the drug delivery device at the skin surface. The command information is encoded digitally and then used to modulate the carrier. The carrier waveform is generated by a means of an oscillating current produced between two electrodes disposed internally and in contact with body fluids. Such a current results in an oscillating dipole electric field that can be sensed externally as the potential difference between two electrodes in contact with the skin. As described below, a preferred embodiment employs as a carrier the same oscillating impedance measuring current used to measure minute ventilation and/or cardiac stroke volume.

The carrier waveform may be modulated with digitally encoded information by a variety of standard modulation techniques such as amplitude shift-keying, frequency shift-keying, phase shift-keying, and M-ary variants of those techniques. Because the impedance between the current injecting electrodes can vary (as, for example, in accordance with cardiac or lung volumes when the electrodes are disposed in a ventricle or elsewhere in the thorax), however, it is preferable to use a modulation technique that is unaffected by changes in the amplitude of the carrier. This is because such impedance variations between the electrodes can affect the potential at the skin surface resulting from a given amplitude of current.

One way to modulate the carrier with the digitally encoded information is to modulate a digital pulse train by varying the frequency, width, or position of the pulses, and then use the modulated pulse train to amplitude modulate the carrier waveform. The pulse train thus constitutes a subcarrier. In a preferred embodiment, the pulse train is frequency modulated in accordance with the digitally encoded information so that the intervals between successive pulses are interpreted as symbols that signify a particular bit in the case of binary symbols, or a particular bit pattern in the case where more than two symbol states are used (i.e., M-ary modulation methods). In the embodiment described in detail below, the interval between each of the pulses of the pulse train is varied between two values to signify either a 1 or a 0. Each measured pulse interval thus constitutes a binary symbol. Alternate embodiments may employ additional intervals as symbol states in order to increase the data transmission rate. Since a pulse must only be sensed above a certain threshold in order to detect a symbol, this modulation scheme is unaffected by amplitude changes in the modulated carrier.

FIG. 1 is a system diagram of a microprocessor-based implantable cardioverter/defibrillator with the capability of also delivering pacing therapy. A microprocessor 10 communicates with a memory 12 and peripheral devices via bidirectional address and data busses. The memory 12 typically comprises a ROM or RAM for program storage and a RAM for data storage. The device has atrial and/or ventricular sensing and pacing channels for sensing depolarizations and delivering pacing pulses to the atria and/or ventricle. Each atrial/ventricular sensing and pacing channel comprises an electrode, lead, sensing amplifier, pulse generator, and a channel interface for communicating with the microprocessor 10, represented in the figure by electrode 24, lead 23, sensing amplifier 21, pulse generator 22, and a channel interface 20. A channel interface includes analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. For each channel, the same lead and electrode are used for both sensing and pacing. The sensing channels are used in conjunction with pacing and for detecting arrhythmias. Also interfaced to the microprocessor is a shock pulse generator 50 for delivering cardioversion or defibrillation pulses to the heart via a pair of electrodes 51a and 51b, and a radio frequency telemetry interface 40 for communicating with an external programmer. A battery (not shown) supplies power to the device.

The device also has the capability of measuring the electrical impedance between electrodes 34a and 34b. A current is injected between the electrodes from constant current source 43, and the voltage between the electrodes is sensed and transmitted to the impedance measurement interface 30 through sense amplifier 31. The impedance measurement interface processes the voltage signal to extract the impedance information therefrom and communicates with the microprocessor. Depending upon where the electrodes 34a and 34b are disposed, the impedance measurement can be used to measure minute ventilation or cardiac stroke volume. An example of the latter is described in U.S. Pat. No. 5,190,035, issued to Salo et al., and hereby incorporated by reference.

In order to communicate command information to the external drug delivery device, a current signal is generated between the electrodes 34a and 34b by driving the constant current source 43 with an oscillator 44. The waveform of the oscillator is modulated by an amplitude shift-keying (ASK) modulator 44 in accordance with the output of data communications interface 40. The data communications interface 40 receives digital data from the microprocessor 10 and frequency modulates a digital pulse train such that the interval between successive pulses is a binary symbol. The frequency modulated pulse train is then used as a subcarrier to modulate the carrier waveform. In this embodiment, the same current is used for both impedance measurement and data transmission to the external drug delivery device. Other embodiments may transmit information with current signals that are not also used for impedance measurement, in which case a constant current is not necessary.

Figure 2:
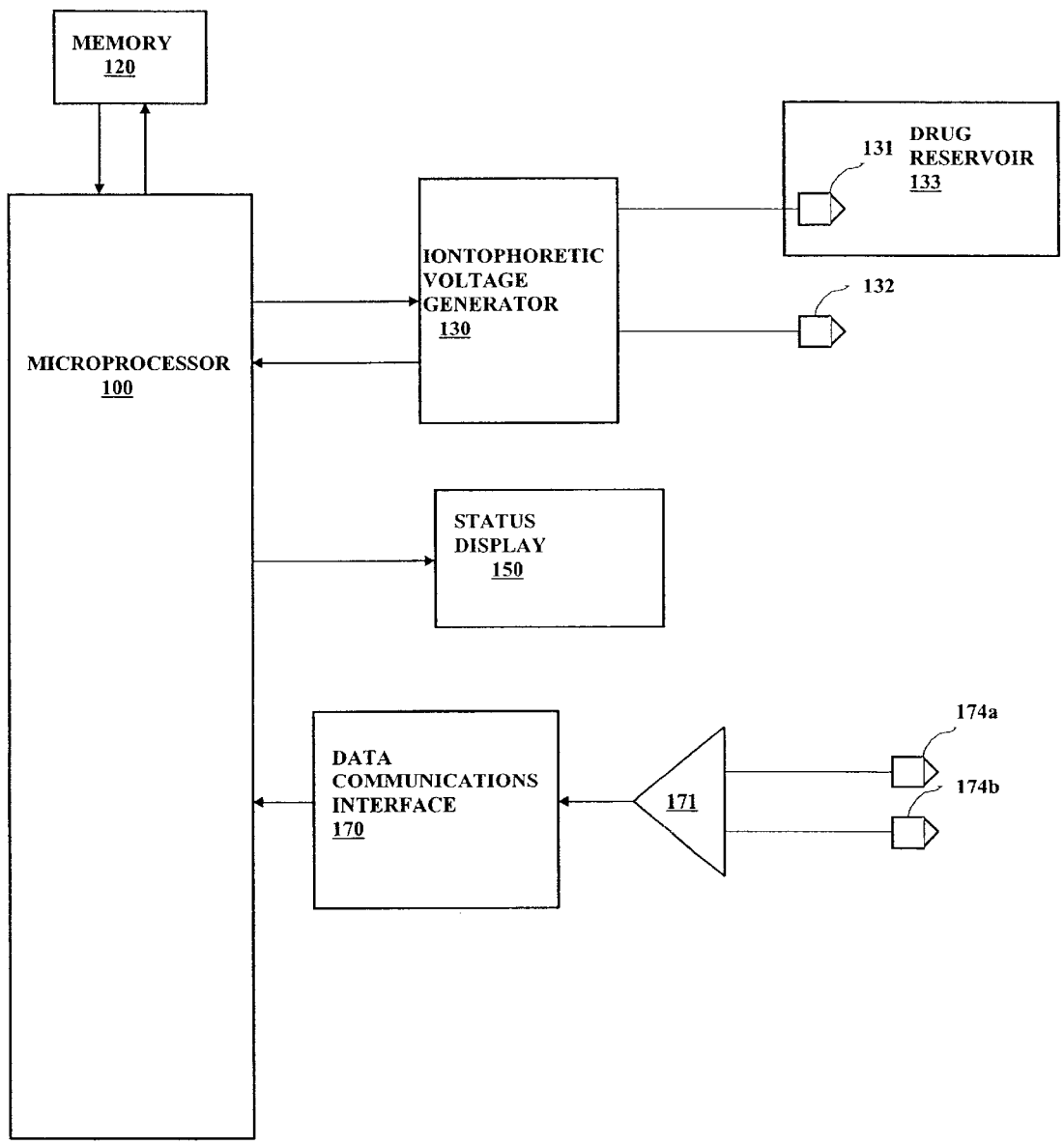
FIG. 2 is system diagram of the drug delivery device.

FIG. 2 is a system diagram of an external drug delivery device for delivering a quantity of a drug in accordance with a command signal received from the implantable cardiac device. The control circuitry of the drug delivery device includes a microprocessor 100 and memory 120. A battery (not shown) supplies power to the device. Interfaced to the microprocessor is a electrically modulated transdermal drug delivery voltage generator 130 for generating a voltage between electrodes 131 and 132. Electrode 131 is electrically connected to a drug reservoir 133 which is adapted for contacting the patient's skin. The term "electrically modulated transdermal drug delivery device" is meant to include any device that uses an electrical field to controllably deliver drugs transdermally such as by e.g., iontophoresis, electroporation, electrorepulsion, or electro-osmosis. Electrode 132 is also adapted for contacting the patient's skin so that when a voltage is impressed across the electrodes, charged drug molecules are caused to migrate from the reservoir 133 through epidermal appendages and pores into the dermal capillary bed where the drug then diffuses into the circulation. The drug may be in the form of an aqueous solution whose pH is adjusted so that most of the drug is in a charged form, with the polarity of the electrodes 131 and 132 adjusted for whether the drug is in anionic or cationic form. The drug solution may then be contained in the reservoir by any medium capable of holding the drug and allowing its free flow when subject to an electrical field such as a gauze patch, or a gel or solution with a porous wrapping. The reservoir 133 is preferably mounted in a frame suitable for affixation to the patient such that the reservoir is in contact with skin. A status display 150 is also interfaced to the microprocessor for displaying information to a user relating to the device's operating status such as battery power remaining, the amount of drug in the reservoir, and a log of previous drug deliveries including the amount of drug delivered.

In order to receive command information from the cardiac device, potentials are sensed at the skin surface between electrodes 174a and 174b by sensing amplifier 171. The output of amplifier 171 is input to data communications interface 170 which demodulates the sensed potentials to derive the digital signal encoded with command information by the cardiac device. The digital signal is then processed by the microprocessor 100 in order to extract the command information contained therein. In this embodiment, the signal transmitted by the cardiac device is a carrier signal ASK modulated with a digital pulse train. The digital pulse train is used as a subcarrier by modulating the frequency of the pulses in accordance with a digital signal encoded with the command information. The time interval between each successive pulse is one of two possible values to indicate a 1 or a 0 and thus constitutes a binary symbol.

Figure 3:
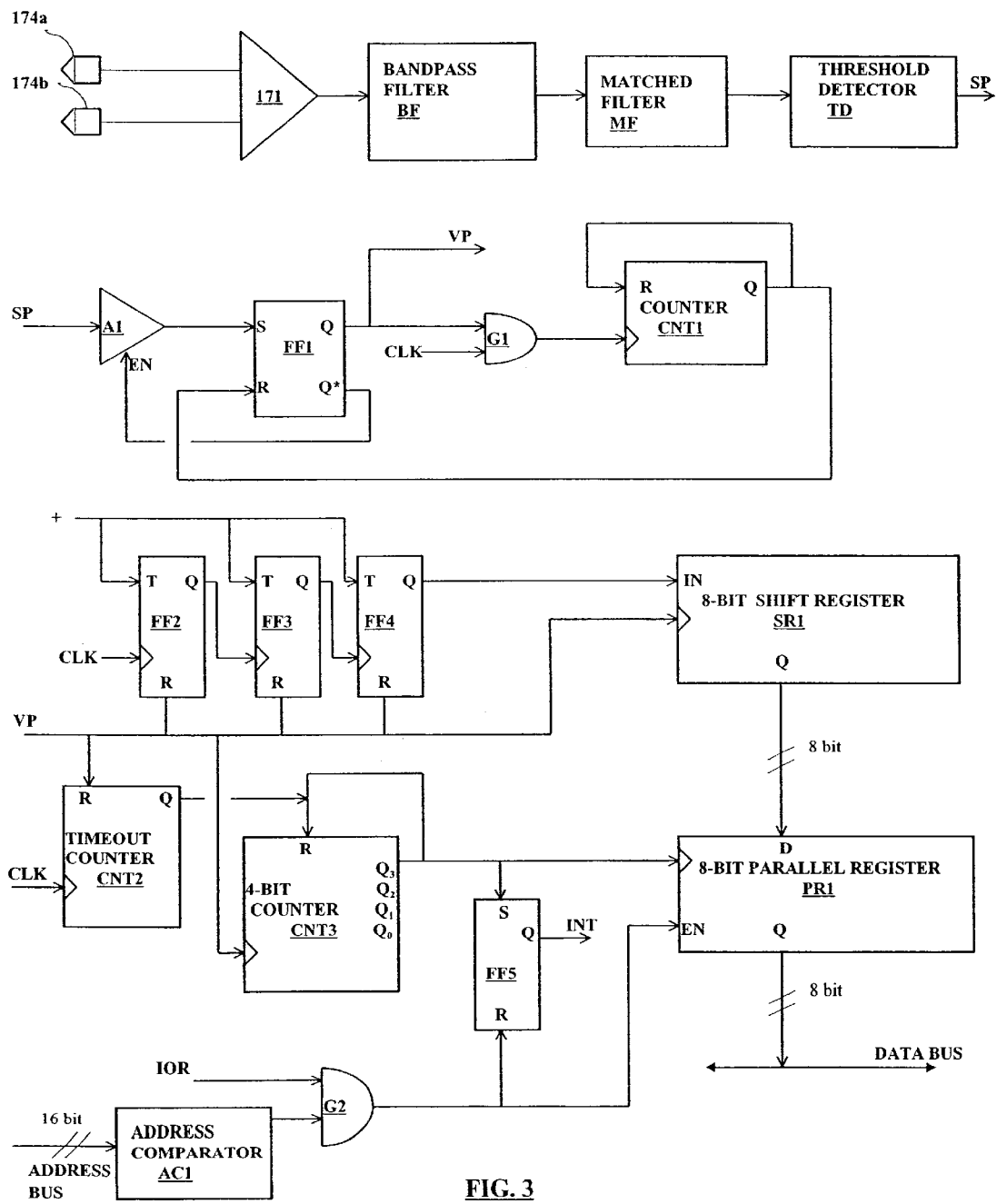
FIG. 3 is a circuit diagram of a data communications interface incorporated into the drug delivery device.

FIG. 3 is a high-level circuit diagram of the data communications interface 170. This particular embodiment uses discrete components to process the sensed potential signals, but the functionality could also be implemented by software executed by the microprocessor 100. The sensed potential signal from amplifier 171 is input to a bandpass filter BF that has its center frequency at the carrier signal frequency. In order to provide further noise immunity, the filtered signal is then input to a matched filter MF. The output of the matched filter MF is essentially a correlation between the sensed signal and a template signal corresponding to a transmitted pulse. The matched filter output is then compared with a specified threshold by threshold detector TD. If the threshold is exceeded, a sensed pulse signal SP compatible with the rest of the digital circuitry is output. The result of these steps is thus the ASK demodulation of the sensed carrier waveform. These operations may be performed by analog components or in the digital domain by processing digitized samples of the sensed signal.

As already noted, the time interval between each transmitted pulse and the preceding transmitted pulse is a symbol indicating either a 0 or a 1. In this embodiment, the interval between each pulse subcarrier pulse train is either T or 2T seconds such that the pulse frequency varies between 1/T and 1/2T Hz. Due to noise, however, the threshold detector TD may output sensed pulse signals separated by a much shorter interval. In order to avoid such spurious signals, only one sensed pulse SP within a specified limit time period is allowed to be regarded as a valid pulse and used to determine the interval symbol. A sensed pulse signal SP is input to a buffer A1 which either passes the signal or not in accordance with its tri-state enable input EN. If buffer A1 is enabled, the SP signal is passed to the set input S of flip-flop FF1. The Q output of FF1 is then asserted as a valid pulse signal VP which is decoded as a 1 or 0 by other circuitry using only the rising edge of VP. VP is maintained high for the limit time period until flip-flop FF1 is reset by the output of counter CNT1. When VP is asserted, AND gate G1 passes clock pulses CLK to the clock input of counter CNT1. When counter CNT1 has counted a number of clock pulses equal to the specified limit time period, the Q output of the counter corresponding to the limit time period is asserted which then resets flip-flop FF1 and the counter itself. Resetting of flip-flop FF1 deasserts the valid pulse signal VP which disables further clocking of counter CNT1 through gate G1 and readies the flip-flop for receipt of another sensed pulse signal SP. In order to ensure that VP is deasserted after timeout of the counter CNT1 so that another rising edge of VP can be output, the complementary output Q* of FF1 is used to tri-state disable the buffer A1 and prevent the setting of flip-flop FF1 until the flip-flop is reset by the Q output of counter CNT1. The rising edges of the signal VP thus correspond to the pulse train subcarrier which has been modulated with the digitally encoded command information.

In order to demodulate the subcarrier, the rising edge of each asserted VP signal is used to detect a transmitted symbol in accordance with whether the time interval elapsed since the previous assertion of VP is T or 2T. In this embodiment, the period of the CLK signal is assumed to be 3T/8 so that the clock frequency is 8/3 times as fast as the fastest symbol rate 1/T of the transmitted signal. Flip-flops FF2, FF3, and FF4 are T-type flip-flops which together make up a divide-by-8 ripple counter clocked by the CLK signal so that the Q output of FF4 is a square wave of period 3T. The ripple counter is reset by each assertion of VP so that the Q output of FF4 transitions from low to high at a time 3T/2 after VP is asserted. This allows the next assertion of VP to use the output of the ripple counter as a data signal corresponding to the interval since the previous assertion of VP. That data signal is then clocked into a shift register SR1. A 0 is clocked into SR1 if the VP signal occurs earlier than time 3T/2 since the previous VP assertion, and a 1 is clocked in if the VP occurs between a time 3T/2 and 3T after the previous VP assertion when the ripple counter output is high. The time 3T/2 thus represents the mid-point between the two interval symbol states T and 2 T. In this way, each VP pulse results in a 1 or a 0 being clocked into the shift register SR1 in accordance with the time interval since the previous VP pulse. Note that if no previous VP pulse has been received, the first VP pulse clocks an indeterminate value into the shift register and should be disregarded.

Shift register SR1 is an 8-bit register so that the register is full after eight VP assertions, and the data contained therein must to transferred elsewhere. Counter CNT3 is a 4-bit counter clocked by the rising edge of VP so that its most significant bit output $Q_3$ is asserted after eight assertions of VP. $Q_3$ is tied to the clock input of 8-bit parallel register PR1 so that its assertion loads the 8-bit output of shift register SR1 into register PR1. Assertion of $Q_3$ also resets the counter CNT3. In this manner, the demodulated data contained in shift register SR1 is transferred to register PR1 after every eight assertions of VP. A timeout counter CNT2 is also clocked by CLK with its Q output corresponding to a specified timeout period used to reset counter CNT3. Thus, in the event that no VP assertion is received after the specified timeout period, the framing of data into 8-bit bytes is restarted with the next VP pulse.

Assertion of $Q_3$ also sets flip-flop FF5 which causes assertion of an interrupt signal INT to the microprocessor signifying that the data contained in register PR1 is available for reading. The interrupt servicing routine then accesses the register PR1 by putting its address on the address bus which causes the output of address comparator AC1 to go high. AND gate G2 then passes the assertion of a read strobe IOR to enable the tri-state outputs of register PR1 and puts its 8-bit contents onto the data bus. The read strobe IOR also resets the flip-flop FF5 to clear the interrupt signal.

Data is thus received by the microprocessor in the form of consecutive 8-bit bytes. Such data can include error-correcting codes in order for the microprocessor to determine whether the data should be regarded as valid command information. The cardiac device may repeat each transmission a specified number of times in order to increase the probability that a valid transmission is received. The data can be segregated into separate frames for this purpose with the beginning and end of each frame signified by particular data bytes.

In operation, the cardiac device detects a particular medical condition such as an arrhythmia by an analysis of the digitized information received from the sensing channels according to algorithms implemented by the programmed microprocessor 10. Upon detection of a particular condition indicating the need for drug delivery, a command signal is generated which consists of a coded message suitable for transmission via the data communications interface 40. The command signal is then used to modulate the carrier signal generated by the current source 43 which is received by the drug delivery device. Upon sensing of the transmitted current signal at the skin surface and demodulation to derive the command signal, the transdermal drug delivery voltage generator 130 is activated by the microprocessor 100 to deliver a quantity of the drug to the patient. The command signal can also contain information relating to the amount of drug that is to be delivered by the drug delivery device and/or the time period over which the delivery is to take place.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for measuring a physiological variable and drug delivery comprising:

applying a constant amplitude current between two implanted excitation electrodes in the form of an oscillating carrier waveform;

measuring a physiological variable as the potential difference between two implanted sense electrodes as the constant amplitude current is applied;

modulating the carrier waveform with command information generated by an implantable medical device to thereby cause corresponding electrical potential signals that can be sensed at a skin surface location;

receiving and demodulating sensed potential signals at a skin surface location;

deriving command information from the demodulated potential signals; and, controlling delivery of a drug from an external drug delivery device in accordance with the command information.

2. The method of claim 1 wherein the drug delivery device delivers the drug by electrically modulated transdermal injection.

3. The method of claim 1 further comprising transmitting the potential signals in the form of a carrier waveform digitally modulated with the digitally encoded command information by varying the amplitude of the carrier waveform.

4. The method of claim 1 further comprising transmitting the potential signals in the form of a carrier waveform digitally modulated with the digitally encoded command information by varying the frequency of the carrier waveform.

5. The method of claim 1 further comprising transmitting the potential signals in the form of a digital pulse train modulated with the digitally encoded information by varying the frequency of the pulses and amplitude modulating a carrier waveform with the modulated pulse train.

6. The method of claim 1 further comprising transmitting the potential signals in the form of a digital pulse train modulated with the digitally encoded information by varying the width of the pulses and amplitude modulating a carrier waveform with the modulated pulse train.

7. The method of claim 1 further comprising transmitting the potential signals in the form of a digital pulse train modulated with the digitally encoded information by varying the position of the pulses and amplitude modulating a carrier waveform with the modulated pulse train.

8. The method of claim 1 further comprising:

sensing electrical activity occurring in a patient's heart and generating sensing signals in accordance therewith;

extracting information from the sensing signals and detecting a particular medical condition from the extracted information; and, modulating the carrier signal with a command signal generated by the implantable medical device and transmitting the command signal to the external drug delivery device if the medical condition is present.

9. The method of claim 1 wherein the potential difference between the sense electrodes when the constant amplitude current is applied reflects transthoracic impedance, and further wherein the measured physiological variable is minute ventilation.

10. The method of claim 1 further comprising delivering the drug from the external delivery device by transdermal injection.

11. The method of claim 1 wherein the potential difference between the sense electrodes when the constant amplitude current is applied reflects transthoracic impedance, and further wherein the measured physiological variable is cardiac stroke volume.

* * * * *

UNITED STATES PATENT AND TRADEMARK OFFICE
CERTIFICATE OF CORRECTION

PATENT NO. : 6,689,117 B2
DATED : February 10, 2004
INVENTOR(S) : Sweeney et al.

It is certified that error appears in the above-identified patent and that said Letters Patent is hereby corrected as shown below:

Title page,
Item [56], References Cited, U.S. PATENT DOCUMENTS, delete "5/1995" and insert -- 6/1995 --, therefor.

Signed and Sealed this

Sixteenth Day of November, 2004

JON W. DUDAS
*Director of the United States Patent and Trademark Office*